(12) United States Patent
O'Neill

(10) Patent No.: US 11,598,700 B2
(45) Date of Patent: Mar. 7, 2023

(54) TISSUE MARKING DYE APPLICATOR, SYSTEM, AND METHOD

(71) Applicant: Cancer Diagnostics, Inc., Durham, NC (US)

(72) Inventor: Patrick O'Neill, Durham, NC (US)

(73) Assignee: Cancer Diagnostics, Inc., Durham, NC (US)

( * ) Notice: Subject to any disclaimer, the term of this patent is extended or adjusted under 35 U.S.C. 154(b) by 534 days.

(21) Appl. No.: 16/401,572

(22) Filed: May 2, 2019

(65) Prior Publication Data

US 2019/0339174 A1 Nov. 7, 2019

Related U.S. Application Data

(60) Provisional application No. 62/666,845, filed on May 4, 2018.

(51) Int. Cl.
  *G01N 1/31* (2006.01)
  *A61B 90/00* (2016.01)
  *C09D 11/00* (2014.01)

(52) U.S. Cl.
  CPC .............. *G01N 1/31* (2013.01); *A61B 90/39* (2016.02); *C09D 11/00* (2013.01)

(58) Field of Classification Search
  CPC .......... C09D 11/00; G01N 1/31; A61B 90/39; A61B 2090/3908; A61B 2090/3937
  See application file for complete search history.

(56) References Cited

U.S. PATENT DOCUMENTS

| | | | | |
|---|---|---|---|---|
| 3,475,105 A | * | 10/1969 | Gerson | B43K 5/1845 401/260 |
| 7,267,669 B2 | * | 9/2007 | Staunton | A61M 5/14228 604/173 |
| 8,301,227 B2 | | 10/2012 | Phillips | |

(Continued)

FOREIGN PATENT DOCUMENTS

WO  2006049962  5/2006

OTHER PUBLICATIONS

3-Way Bulb. 3-Way Bulb: Description, (n.d.). https://www.chemedx.org/JCESoft/jcesoftSubscriber/ChemPagesLab/modules/bulb3way/bulb3waydesc.htm. (Year: 2021).*

(Continued)

*Primary Examiner* — Samuel P Siefke
*Assistant Examiner* — Tingchen Shi
(74) *Attorney, Agent, or Firm* — Fitch, Even, Tabin & Flannery LLP

(57) ABSTRACT

In one aspect of the present disclosure, a tissue marking system is provided that includes a container and an applicator. The applicator is in the container and is removable therefrom. The applicator includes a tip, a reservoir containing sterile tissue marking dye, and a valve. The valve is configured to open and permit sterile tissue marking dye to flow from the reservoir to the tip of the applicator in response to the tip being pressed against a priming surface. In one embodiment, the system includes a substrate that is removable from the container and includes the priming surface. In another embodiment, the container includes a tray having a compartment that receives the applicator. The tray includes a well that includes the priming surface.

22 Claims, 12 Drawing Sheets

(56) References Cited

U.S. PATENT DOCUMENTS

| | | | | |
|---|---|---|---|---|
| 8,594,768 | B2* | 11/2013 | Phillips | A61B 90/39 |
| | | | | 600/424 |
| 8,750,966 | B2 | 6/2014 | Phillips | |
| 9,044,268 | B2 | 6/2015 | Phillips | |
| 9,055,803 | B2 | 6/2015 | Purizhansky | |
| 10,238,465 | B1 | 3/2019 | Phillips | |
| 10,507,077 | B2 | 12/2019 | Phillips | |
| 2004/0190975 | A1* | 9/2004 | Goodman | B05C 17/002 |
| | | | | 401/134 |
| 2006/0090658 | A1 | 5/2006 | Phillips | |
| 2008/0028962 | A1 | 2/2008 | Phillips | |
| 2008/0068707 | A1* | 3/2008 | Goodman | G01N 1/31 |
| | | | | 359/368 |
| 2008/0071208 | A1* | 3/2008 | Voegele | A61B 17/062 |
| | | | | 604/57 |
| 2010/0233791 | A1* | 9/2010 | Sim | B01L 3/502715 |
| | | | | 435/286.4 |
| 2013/0071858 | A1* | 3/2013 | Bui | G01N 35/00732 |
| | | | | 435/7.21 |
| 2013/0157381 | A1* | 6/2013 | Pang | G01N 33/53 |
| | | | | 436/501 |
| 2014/0079604 | A1* | 3/2014 | O'Neill | G01N 1/31 |
| | | | | 422/536 |

OTHER PUBLICATIONS

Pipetman L P20L, 2-20 μL, Metal Ejector. Gilson, (n.d.). https://www.gilson.com/default/pipetman-l-p20l-2-20-micro-l-metal-ejector.html. (Year: 2021).*

Paula Heimler. (2012). Choosing the Best Pipette Tip for your Application. Thermo Fisher. (Year: 2012).*

Beekley Corporation; List of Beekley Medical® Specimen Radiography products; accessed May 2, 2019; 6 pages.

Cancer Diagnostics, Inc.; CDI's® Tissue Marking Dyes—Specimen Processing; Mar. 10, 2015; 1 page.

Cancer Diagnostics, Inc.; Guidelines for Marking & Mapping Specimens; Feb. 26, 2015; 2 pages.

Phillips, Michael J et al., Tissue Marking System, abandoned U.S. Appl. No. 13/838,568, filed Mar. 15, 2013.

* cited by examiner

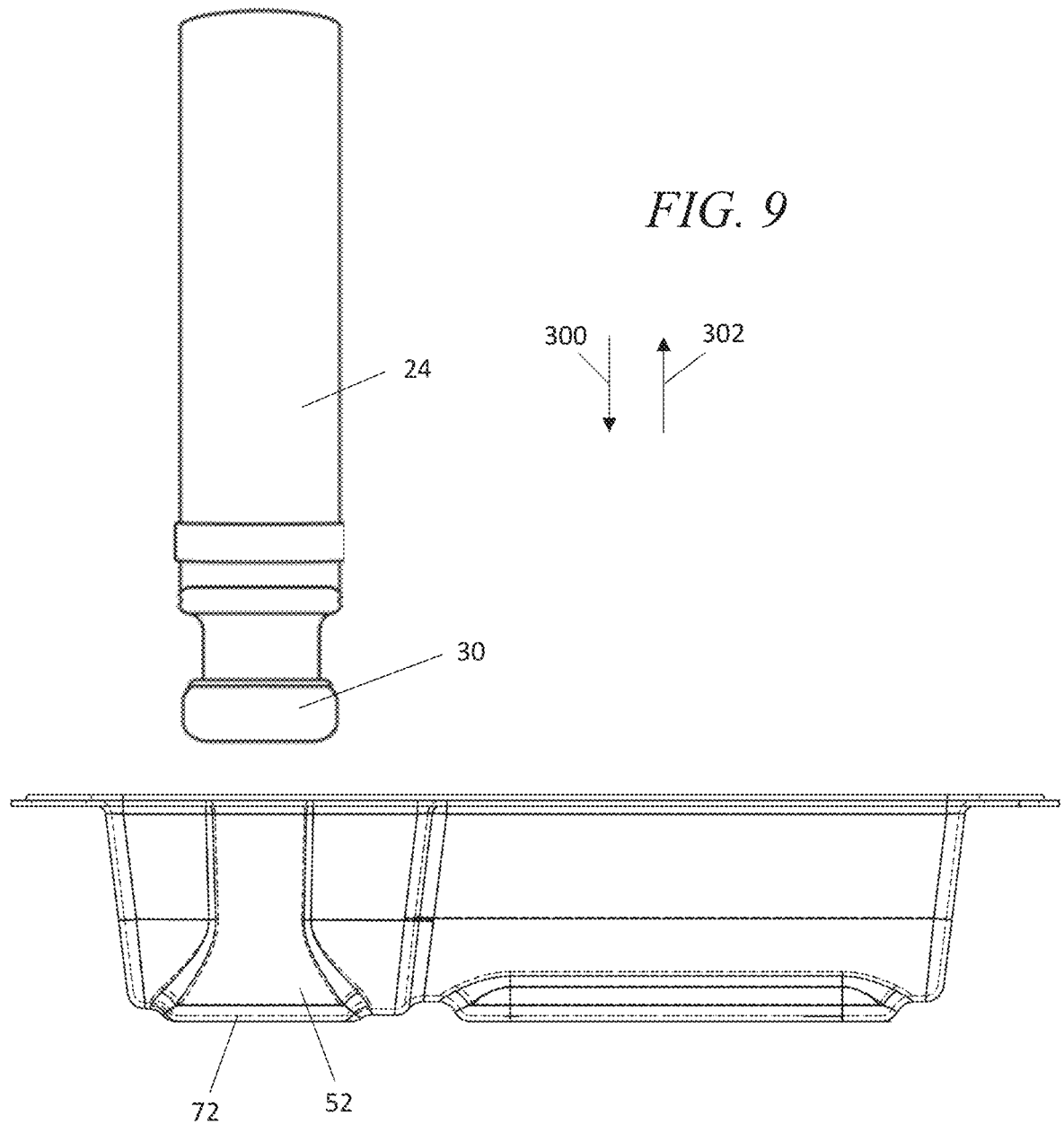

TISSUE MARKING DYE APPLICATOR, SYSTEM, AND METHOD

CROSS-REFERENCE TO RELATED APPLICATION

This application claims the benefit of U.S. Provisional Application No. 62/666,845, filed May 4, 2018, which is incorporated herein by reference in its entirety.

FIELD

This disclosure relates to processing tissue samples and, more particularly, to marking tissue samples with ink or dye to identify the orientation of the tissue sample removed during surgery to help define the margins of excised tissue.

BACKGROUND

A tissue sample may be taken from a patient during surgery for examination. For example, a cancerous tumor may be removed from a patient and examined. The tissue sample may be cut into histological blocks and placed in cassettes. The histological blocks are treated with various chemicals, sliced using a microtome, and analyzed using microscopy. The tissue sample may be examined to determine whether the removed tissue has a sufficient margin surrounding the tumor. A margin may be an edge or border of tissue removed during cancer surgery. If there is an insufficient margin, the surgeon may have to perform another surgery to remove additional tissue.

Tissue marking inks may be used to identify the orientation of the tissue sample relative to the patient. A surgeon may apply a different colored marking ink to each surface of the tissue sample with each color indicating a different orientation of the respective surface. For example, the surgeon may mark the medial surface of a tissue sample with red ink and the anterior surface of the tissue sample with yellow ink. If the analysis of the tissue sample indicates there is an insufficient margin at the medial surface, the surgeon may perform another surgery to remove additional tissue in the patient in a medial direction to ensure sufficient tissue has been removed.

One prior tissue marking system includes a kit having a tray defining three or more reservoirs for different colored inks. The kit is a commercial embodiment of disclosures of U.S. Pat. No. 9,044,268. The kit further includes three or more applicator tools each having a sponge and a handle connected to the sponge. A surgeon marks a tissue sample by removing one of the tools from the tray, pressing the sponge thereof into one of the reservoirs to absorb ink in the reservoir, and then pressing the ink-soaked sponge against one of the surfaces of a tissue sample. The surgeon then repeats this process using a tool and a reservoir for each surface of the tissue sample the surgeon wants to mark.

One problem with this approach is that the inks may spill out from their reservoirs, such as into a nearby reservoir, if the tray is bumped. Each reservoir has walls surrounding the reservoir and a large upper opening defined by the walls that allows the sponge of one of the applicator tools to be advanced into the reservoir for soaking. Although the large openings of the reservoirs allow easy access for the applicator tool sponges, the large openings also limit the ability of the reservoirs to resist egress of inks from the reservoirs.

The '268 patent discloses that, in one embodiment, an ink absorbent material such as foam or felt is provided in each of the reservoirs to absorb and hold the ink. One shortcoming of the commercial application of this approach is that some of the ink colors, such as green, blue, and black, may all look similar in the reservoirs.

Another problem with the approach of the '268 patent is that a surgeon may want to use ink colors different than those provided in the kit. To provide surgeons with additional ink colors to choose from, the number of ink reservoirs and applicator tools is increased. The downside of providing a larger number of ink reservoirs, such as six, that a surgeon may select from is that the surgeon may use fewer than all of the colors for a particular tissue sample. The unused colors and applicator tools are discarded with the kit after the surgical procedure. Thus, although kits having many ink colors provide additional flexibility for a surgeon, some of the colors may not be used which creates waste once the kit is discarded after the surgical procedure.

SUMMARY

In accordance with one aspect of the present disclosure, a tissue marking system is provided that includes a container and an applicator. The applicator is in the container and is removable therefrom. The applicator includes a tip, a reservoir containing sterile tissue marking dye, and a valve. The valve is configured to open and permit sterile tissue marking dye to flow from the reservoir to the tip of the applicator in response to the tip being pressed against a priming surface. The system provides a self-contained, ready-to-use applicator for applying sterile tissue marking dye stored in the reservoir of the applicator to a surface of a tissue sample. The applicator may be easier to use than some prior techniques since a surgeon uses the applicator to apply sterile tissue marking dye within the applicator to a tissue sample surface rather than having to first transfer ink in a reservoir to a separate applicator tool and then transfer the ink from the applicator tool to the tissue sample surface as discussed in U.S. Pat. No. 9,044,268.

In one form, the tissue marking system includes a substrate that includes the priming surface and is removable from the container. To sterilize the tissue marking dye, the container with the applicator therein is sterilized, such as by gamma irradiation, which renders the interior of the container sterile for operating room purposes including the applicator, the tissue marking dye, and the substrate within the interior of the container. Although the exterior of the container is sterilized, the container is subsequently shipped and handled which makes the exterior of the container non-sterile for operating room purposes. Once the container has been provided in an operating room, the applicator and substrate may be removed from the container, the substrate placed on a sterile surface of an operating room, and the tip of the applicator is pressed against the substrate to cause sterile tissue marking dye to flow into the tip of the applicator. This primes the applicator for applying the sterile tissue marking dye to a surface of a tissue sample. Further, because the surgeon can press the applicator tip against the substrate, which may be resting on a sterile operating room tray, the surgeon can apply a firmer force on the applicator to initiate the flow of tissue marking dye into the applicator tip and can apply a softer force on the applicator to transfer dye from the tip to a surface of a tissue sample.

In one form, the container includes a well sized to receive the tip of the applicator and a base wall that includes the priming surface. In this manner, the well of the container can be used to initiate flow of sterile tissue marking dye to the applicator tip and capture any excess sterile tissue marking dye from the tip. Once the tip has been infused with a desired amount of sterile tissue marking dye, the surgeon may use the applicator to mark a surface of a tissue sample with the tissue marking dye. The container thereby holds the applicator until the container is opened, then the container well may be used to cause tissue marking dye to flow to the applicator tip. Further, the container and applicator therein are sterilized such as by using gamma irradiation, so that the applicator and tissue marking dye therein are sterile for use in an operating room. The sterilization process renders the interior of the container sterile such that the base wall of the well provides a sterile surface against which the applicator tip may be pressed to initiate the flow of tissue marking dye into the applicator tip.

The well may also include at least one wall upstanding from the base wall to resist egress of sterile tissue marking dye from the well. This resists excess tissue marking dye in the well from flowing outward therefrom and into another portion of the container, which keeps the excess tissue marking dye in the well ready to be absorbed by the applicator tip.

A plurality of tissue marking systems may be provided to a surgeon with each system including an applicator having a different colored tissue marking dye. The surgeon may only open the containers of the systems having the sterile tissue marking dye colors desired by the surgeon. The unused systems may be saved for later use. In this manner, the system reduces waste because unused tissue marking dyes need not be discarded.

In accordance with another aspect of the present disclosure, a method of marking a tissue specimen is provided that includes opening a container and removing an applicator from the container. The method includes opening a valve of the applicator by contacting a tip of the applicator with a priming surface to cause a first sterile tissue marking dye in a reservoir of the applicator to flow to the applicator tip. The method further includes marking a first surface of a tissue sample with the first sterile tissue marking dye of the applicator tip. Because the method includes opening the valve of the applicator by contacting the tip of the applicator with a priming surface, the method provides a surgeon with precise control of providing the first sterile tissue marking dye to the applicator tip.

In one form, the method further comprises removing a substrate that includes the priming surface from the container and positioning the substrate on a surface. The container may have been sterilized, such as by gamma irradiation, such that the applicator and substrate within the container are sterile. The sterile applicator and substrate are removed from the container at a non-sterile area, such as a table in a periphery of an operating room, and the substrate is positioned on a sterile surface in the operating room, such as a tray near the surgical field. The method further includes opening the valve of the applicator by contacting the applicator with the priming surface of the substrate. The method thereby permits a user, such as a surgeon, to infuse the tip of the applicator with sterile tissue marking dye at a sterile location in an operating room using the substrate from within the container.

In another form, opening the valve of the applicator by contacting the tip of the applicator with the priming surface includes advancing at least a portion of the tip into a well of a tray of the container. A surgeon may thereby use the well to prime the applicator tip with the first tissue marking dye before marking the first surface of the tissue sample with the first tissue marking dye of the applicator tip.

BRIEF DESCRIPTION OF THE DRAWINGS

FIG. 9 is a side elevational view of the tip of the tissue marking dye applicator being advanced into the well of the tray;

DETAILED DESCRIPTION

Figure 1:
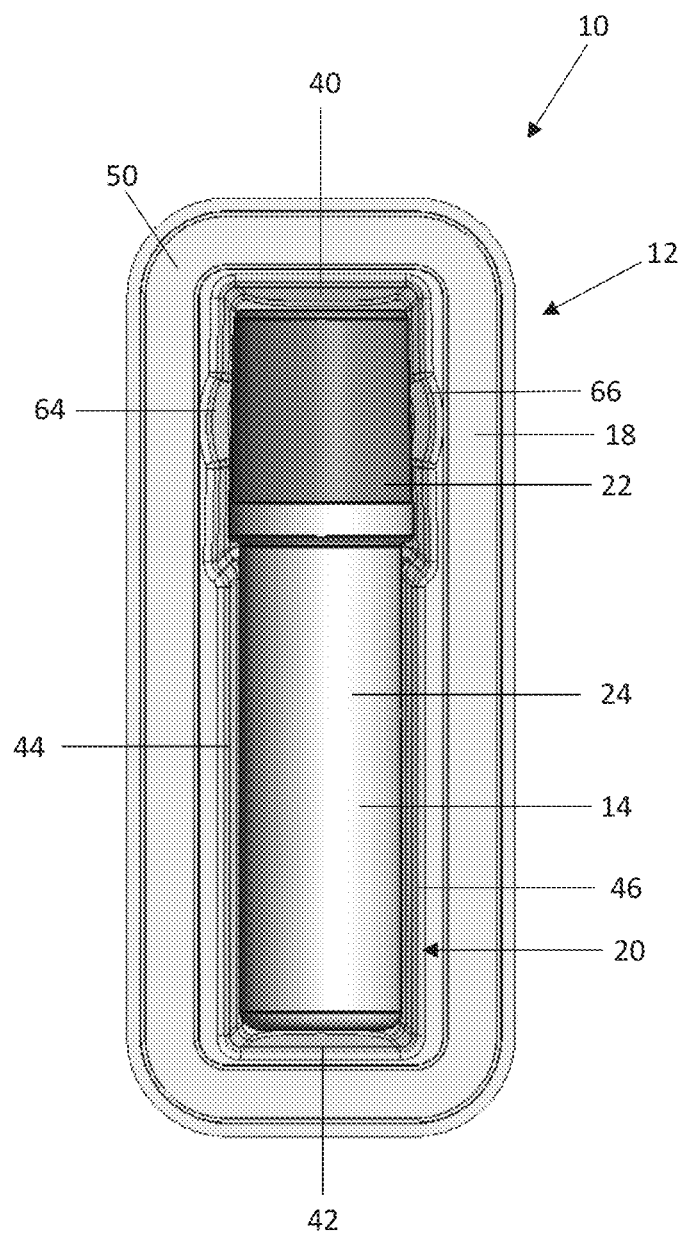
FIG. 1 is a top plan view of a tissue marking system including a container and a tissue marking dye applicator in the container.

With reference to FIG. 1, a tissue marking system 10 is provided that includes a container 12 and an applicator 14 therein for applying sterile tissue marking dye. The container 12 includes a lid 16 (see FIG. 2) and a tray 18 having a compartment 20. The lid 16 may be removed from the tray 18 and the tissue marking dye applicator 14 removed from the compartment 20. The applicator 14 includes a cap 22 and a body 24, and the cap 22 may be removed from the body 24 to expose a tip of the applicator 14 such as a pad 30 (see FIG. 6). The body 24 includes a reservoir 26 (see FIG. 7) that contains tissue marking dye 27. The pad 30 may be pressed against a surface of a tissue sample to transfer tissue marking dye 27 from the reservoir 26 to the surface of the tissue sample. In this manner, the tissue marking system 10 provides an easy-to-use approach for applying the tissue marking dye 27 to a surface of a tissue sample. The tissue marking system 10 reduces waste because, if multiple systems 10 are provided with each system 10 containing an applicator 14 with a differently colored tissue marking dye 27, a surgeon may only use the tissue marking systems 10 having the surgeon's desired tissue marking dye colors. Unused tissue marking systems 10 associated with unused tissue marking dye colors may be saved for later use, which avoids discarding of unused tissue marking dyes 27. Further, because the tissue marking dye 27 is contained in the reservoir 26 of the applicator body 24, spillage of tissue marking dye 27 is limited. The applicator 14 provides an accurate, controlled approach for applying tissue marking dye 27 to a surface of a tissue sample.

With reference to FIG. 1, the compartment 20 of the tray includes one or more side walls 40, 42, 44, 46. The side walls 40, 42, 44, 46 may be configured to closely conform to the shape of the applicator 14 to limit movement of the applicator 14 within the compartment 20 while permitting the applicator 14 to be removed from the compartment 20. The tray 18 includes a flange 50 extending outward from the tray side walls 40, 42, 44, 46. In one form, the lid 16 is made of a flexible plastic material, such as Tyvek®, and the tray 18 is made of a rigid plastic material, such as polyethylene terephthalate (PETE). The materials of the applicator 14, lid 16, and tray 18 may be selected to permit the system 10 to be sterilized after assembly, such as by using gamma irradiation sterilization. The sterilization procedure renders sterile the applicator 14 and the tissue marking dye 27 therein such that the applicator 14 may be used by a surgeon to apply the tissue marking dye 27 to a tissue sample in an operating room. The system 10 may then be provided to an operating room and, once the lid 16 has been removed, the applicator 14 and the tissue marking dye 27 therein are sterile and ready to be used in the operating room. Further, the lid 16 and/or the tray 18 may be transparent to permit the surgeon to visually check an indicium on the exterior of the applicator 14, such as a color of the cap 22, and confirm the applicator 14 contains the desired color of tissue marking dye 27.

Figure 2:
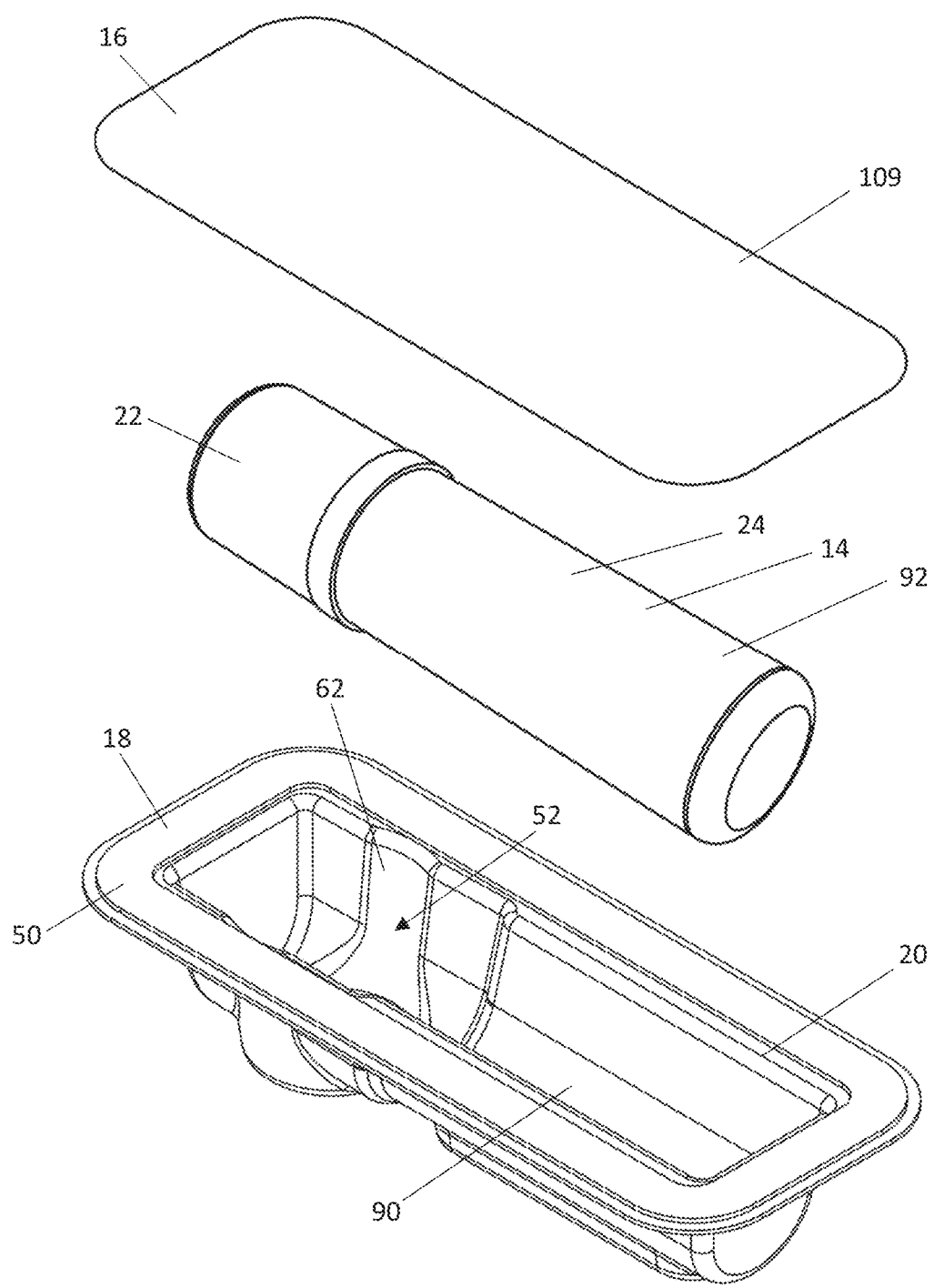
FIG. 2 is an exploded, perspective view of the tissue marking system of FIG. 1 showing the tissue marking dye applicator as well as a lid and a tray of the container.
Figure 3:
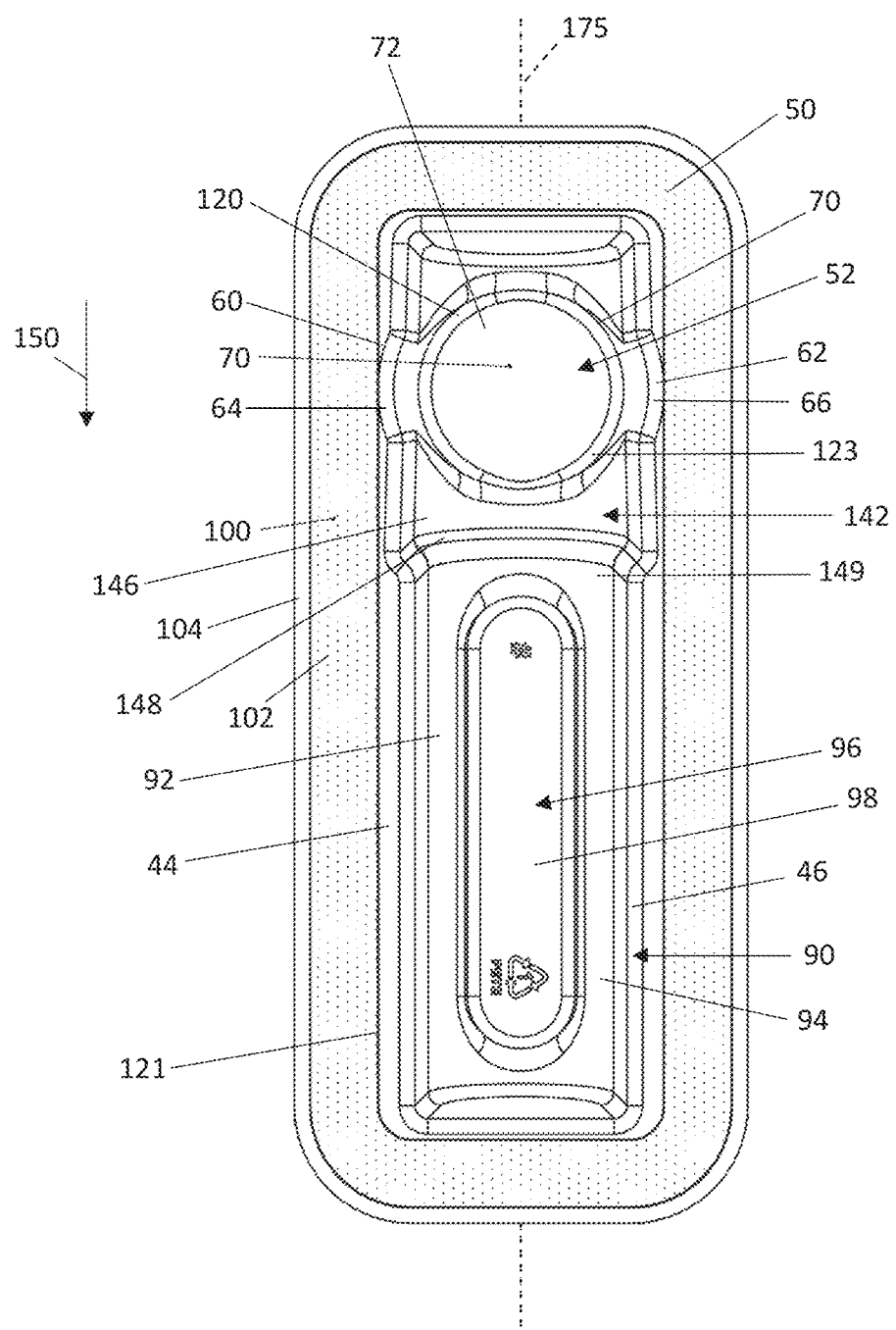
FIG. 3 is a top plan view of the tray of FIG. 2 showing a well of the tray into which a tip of the tissue marking dye applicator may be advanced and pressed to cause tissue marking dye to flow from a reservoir of the applicator into the tip of the applicator.

With reference to FIGS. 2 and 3, the compartment 20 includes a well 52 and the side walls 44, 46 include concave wall portions 60, 62 at the well 52. The wall portions 60, 62 define recesses 64, 66 on opposite sides of the applicator cap 22 (see FIG. 1). The well 52 includes a base wall 70 having a flat inner surface 72. In one form, the inner surface 72 has a shape that matches the shape of a distal surface 208 of the applicator pad 30 (see FIG. 6). For example, the inner surface 72 and the distal surface 208 may be circular with the diameter of the inner surface 72 being slightly larger than the diameter of the distal surface 208. In this manner, a surgeon may hold the applicator 14 upright so that the pad 30 is below the body 24 and advance the pad 30 in direction 300 (see FIG. 9) into the well 52 and into contact with the inner surface 72. As discussed in greater detail below, the applicator 14 may include a valve 80 (see FIG. 8) configured to open in response to the pad 30 being pressed against the inner surface 72. In response to the valve 80 opening, tissue marking dye 27 may flow through a port 82 of the valve 80 from the internal reservoir 26 to the pad 30. The surgeon may hold the pad 30 against the inner surface 72 until the pad 30 contains a desired amount of tissue marking dye 27. Once the desired saturation has been reached, the surgeon may withdraw the pad 30 from the well 52 and then put the pad 30 into contact with a surface of a tissue sample which thereby transfers the tissue marking dye 27 to the tissue sample surface. Because the container 12 has been sterilized, the interior of the container 10 including the inner surface 72 is sterile for operating room purposes. The inner surface 72 provides a sterile surface for the surgeon to press the pad 30 against and trigger the flow of tissue marking dye 27 from the reservoir 26. Further, as shown in FIG. 3, the wall portions 60, 62 have a curved shape which helps guide the pad 30 into contact with the inner surface 72 as the surgeon advances the pad 30 into the well 52 of the tray 18.

With reference to FIG. 3, the tray 20 includes a handle-receiving receptacle 90 of the compartment 20 configured to receive a handle portion 92 (see FIG. 2) of the applicator 14. The handle-receiving receptacle 90 includes inwardly curving portions 92, 94 of the side walls 44, 46. The handle receiving receptacle 90 of the compartment 20 may also include a pocket 96 that extends downward (into the page in FIG. 3) to a floor 98. The base wall 70 of the well 52 and the floor 98 of the handle-receiving receptacle 90 provide a pair of spaced apart, flat feet of the tray 18 that form a bottom of the tray 18 so that the tray 18 stands upright when placed on a surface, such as an operating room table.

Figure 4:
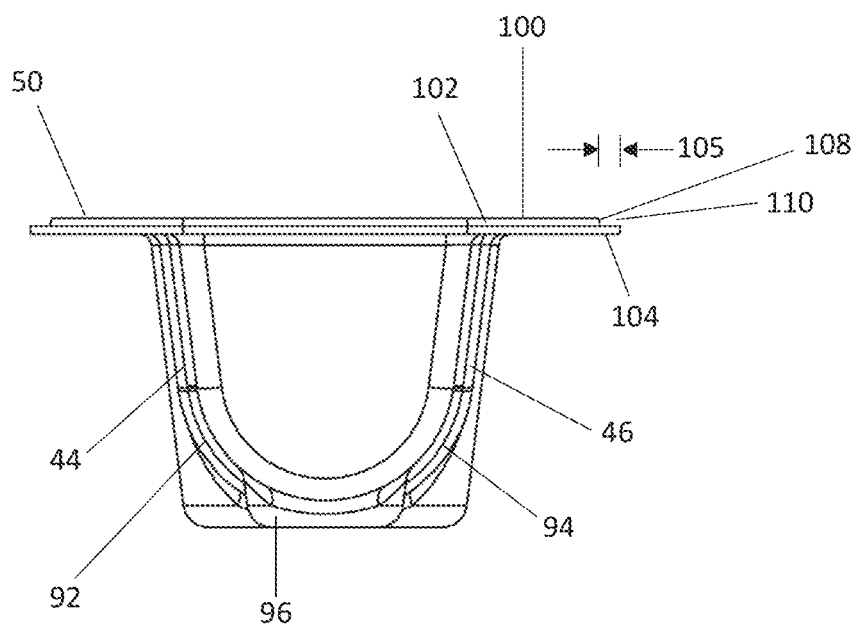
FIG. 4 is an end elevational view of the tray of FIG. 2 showing curved side walls of the tray that support the tissue marking dye applicator.

With reference to FIGS. 2 and 3, the lid 16 may be a flexible, plastic film that is adhered or welded to a sealing surface 100 of the flange 50. The lid 16 may be sealed to the flange 50 to maintain the sterility of the applicator 14 within the compartment 20. The flange 50 may include an inner portion 102 having the sealing surface 100 thereon and an outer portion 104 that is vertically offset from the inner portion 102 and does not include the sealing surface 100 thereon. With reference to FIG. 4, the outer portion 104 is lower than the inner portion 102 and extends outward a distance 105 beyond a peripheral edge 108 of the upper portion 102 and forms a notch 110 at the periphery of the flange 50. The lid 16 is sized so that the lid 16 extends outward beyond the peripheral edge 108 of the upper portion 102 and overlies the lower portion 104. Due to the notch 110, there is a small gap between a periphery 109 (see FIG. 2) of the lid 16 and the lower portion 104. This gap provides a space for a surgical technician to grip an underside of the periphery 109 of the lid 16 and pull the lid 16 off of the tray 18 even if the surgical technician is wearing surgical gloves.

Figure 5:
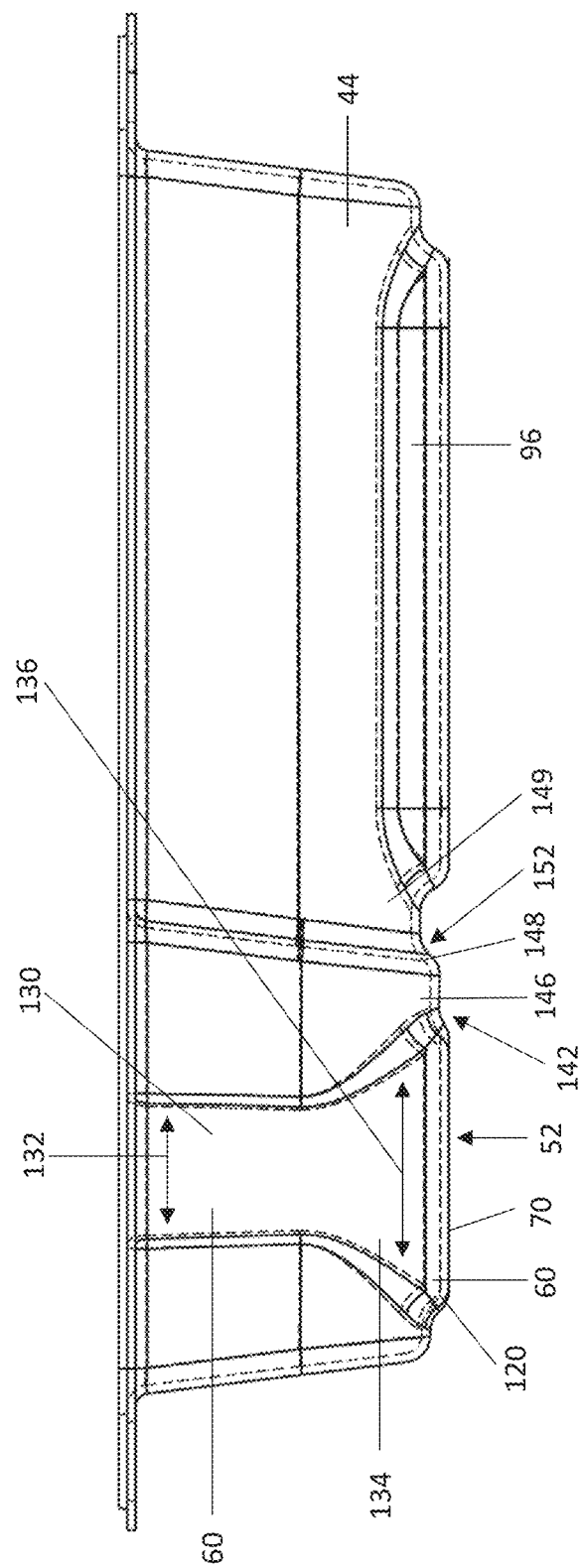
FIG. 5 is a side elevational view of the tray of FIG. 2 showing a raised collar portion of the tray separating the well of the tray and a receptacle of the tray that receives a handle of the tissue marking dye applicator.

As shown in FIGS. 3 and 5, the well 52 includes arcuate walls 120 upstanding from the base wall 70 and extending between the recesses 64, 66 on opposite sides of the well 52. When the applicator pad 30 is pressed against the inner surface 72 of the well 52 to cause tissue marking dye 27 to flow into the applicator pad 30, excess tissue marking dye 27 may transfer from the pad 30 to the inner surface 72. The annular walls 120 keep the tissue marking dye 27 transferred to the inner surface 72 from traveling out of the well 52.

As shown in FIG. 3, the flange 50 of the tray 18 extends about an opening 121 of the compartment 20. The opening 121 is sized to permit the applicator 14 to be withdrawn from the compartment 20. The well 52 includes an upper opening 123 that is smaller than the compartment opening 121 but sufficiently large to permit pad 30 to be advanced into the well 52. The pad 30 may be advanced into the well 50 so that only a distal portion of the pad 30 is disposed in the well 52. In another form, the well 52 is sized to permit the entire pad 30 to be disposed in the well 52.

With reference to FIG. 5, the wall portions 60, 62 of the side walls 44, 46 may have an upper portion 130 with a first width 132 along the side walls 44, 46 and a lower portion 134 with a second width 136 that is larger than the first width 132. The narrower upper portion 130 provides a visual guide for the surgeon to direct the pad 30 into the well 52. The lower portions 134 taper outwardly to the annular wall 120 and direct tissue marking dye 27 that ends up on the wall portions 60, 62 back into the well 52.

Figure 6:
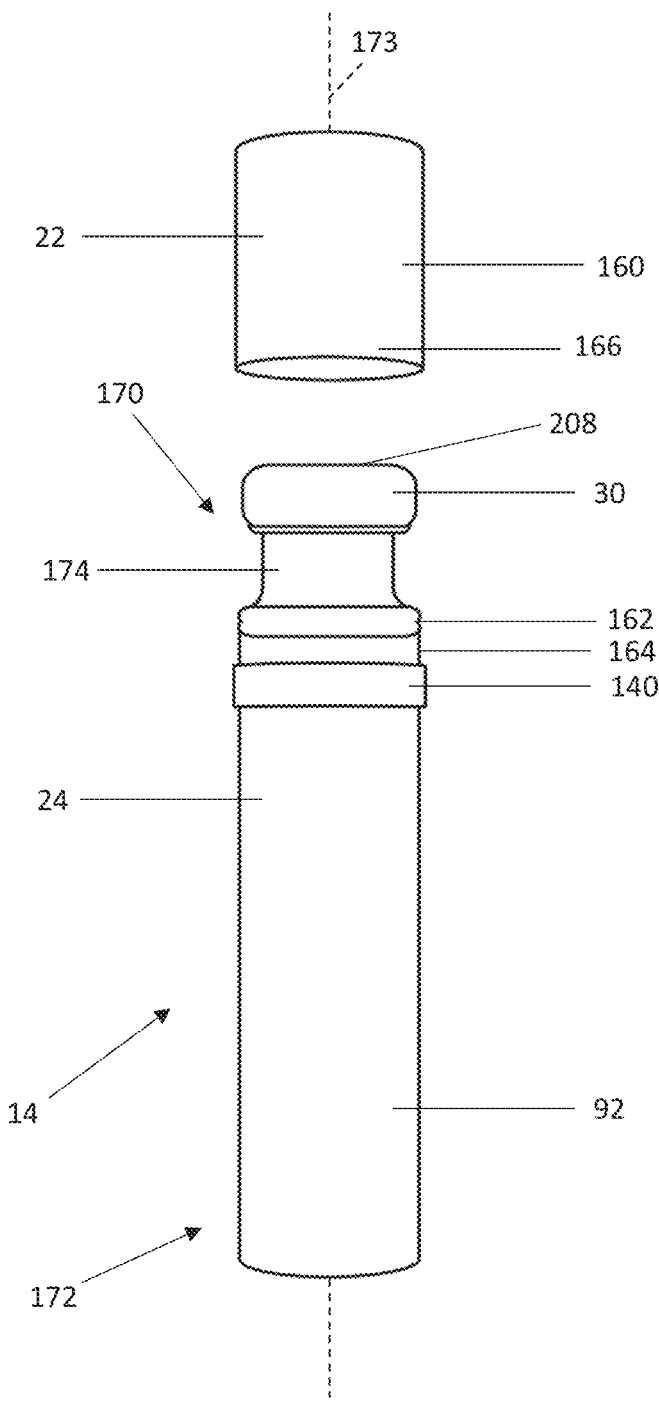
FIG. 6 is an exploded, perspective view of the applicator of FIG. 1 showing a cap of the tissue marking dye applicator removed from a body of the applicator to expose the applicator tip.

With reference to FIGS. 3, 5, and 6, the applicator body 24 includes a rib 140 and the compartment 20 includes a collar portion 142 that receives the rib 140. The collar portion 142 includes a curved lower wall 146 and a neckdown portion, such as a U-shaped wall 148 that tapers inwardly from the curved lower wall 146 to a U-shaped wall 149 for extending around the applicator handle portion 92. The collar portion 142 provides multiple functions. In one respect, the wall 148 of the collar portion 142 resists movement of the rib 140 in direction 150 (see FIG. 3) which keeps the cap 22 and the pad 30 generally disposed above the well 52 when the applicator 14 is in the container 12. The collar portion 142 also creates a step 152 (see FIG. 5) in the bottom of the tray 18. The step 152 separates the well 52 from the pocket 96 of the tray 18. This step 152 further restricts movement of excess tissue marking dye 27 from the well 120 into the pocket 96. Thus, the tissue marking dye 27 that may be left in the well 52 from the applicator pad 30 tends to stay in the well 52 until the tray 18 is disposed of Disposal may include throwing away the used applicator 14 and tray 18 or recycling one or more of the applicator 14, lid 16, and tray 18. In one embodiment, the tray 18 is formed using injection molding a plastic material and has an integral, one-piece construction.

With reference to FIG. 6, the applicator 12 is shown with the cap 22 removed from the body 24. The cap 22 includes a skirt 160 that engages a rib 162 of the body 24. The skirt 160 may have an annular shape and includes an inner diameter that is slightly smaller than an outer diameter of the rib 162 so that there is an interference fit between the skirt 160 and the rib 162. This resists the cap 22 from unintentionally disconnecting from the body 24. The body 24 also includes a channel 164 intermediate the ribs 162, 140. The channel 164 provides a relief for a rim 166 of the skirt 160. The relief provided by the channel 164 permits the rim 166 to deflect radially inward after being urged outwardly by the rib 162 as the cap 22 is connected to the body 24. This relief contributes to a strong connection between the cap 22 and the body 24 because the skirt 160 has areas of lower stress on both sides of the rib 162 when the cap 22 is connected to the body 24.

With reference to FIG. 6, the applicator 14 includes a distal end portion 170, which includes the pad 130, and a proximal end portion 172. The applicator 14 may have a longitudinal axis 173 and the applicator 14 may be elongated along the longitudinal axis 173. The compartment 20 of the tray 18 also includes a longitudinal axis 175 (see FIG. 3) with the axes 173, 175 extending parallel to each other with the applicator 14 received in the compartment 20. In one embodiment, the applicator 14 is a marker. The handle portion 92 has a length sufficient to permit the applicator body 24 to be easily held and maneuvered like a conventional marker.

Figure 7:
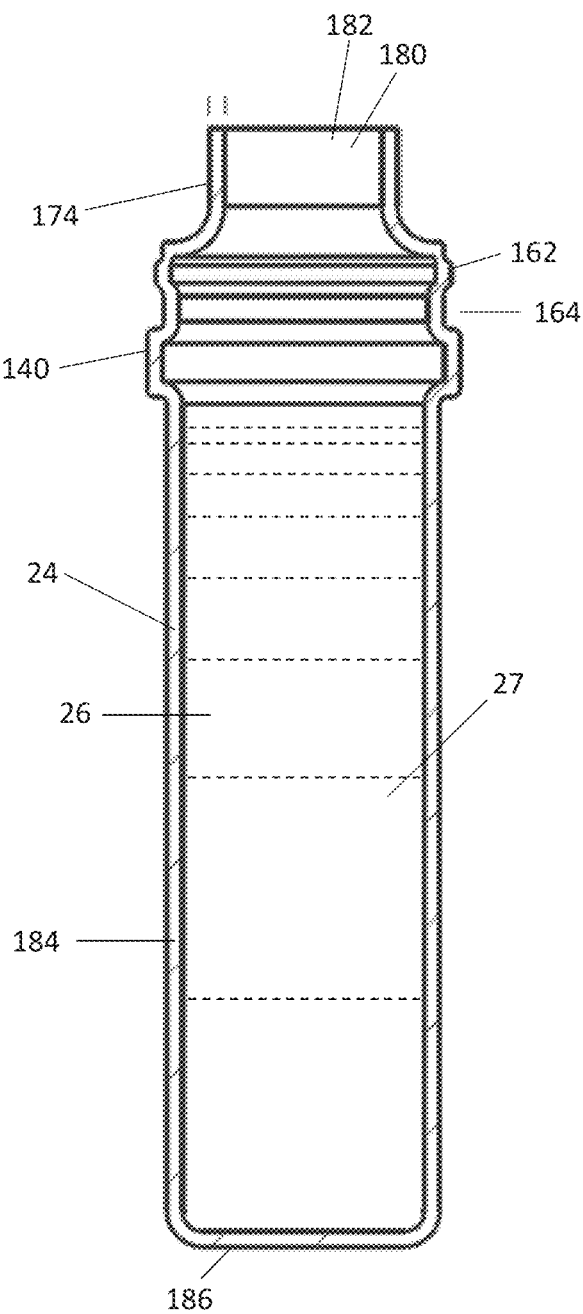
FIG. 7 is a cross-sectional view of the body of the applicator of FIG. 6 showing a reservoir of the body containing tissue marking dye.

With reference to FIG. 7, the distal end portion 170 of the body 24 includes a neck 174 that tapers outwardly to the rib 162. The neck 174 forms a socket 180 and an opening 182 that opens to the socket 180. The body 24 includes a side wall 184, which may be annular, and an end wall 186. The body 24 may be made of a plastic material, and, in one form, may be made from high density polyethylene (HDPE). The body 24 may be formed by injection molding a plastic material, and may have an integral, one-piece construction.

The reservoir 26 may be filled or partially filled with the tissue marking dye 27 when the applicator 14 is sealed in the container 10. In FIG. 7, the body 24 and tissue marking dye 27 are shown in isolation to show the rib 140, rib 162, channel 164, and neck 174 of the body 24. Further, the reservoir 26 is shown partially filled with tissue marking dye 27 as an example. The reservoir 26 may be filled with more or less tissue marking dye 27 as desired for a particular application. Further, as the applicator 14 is used to apply the tissue marking dye 27 to a tissue sample, the valve 80 may permit air to enter the reservoir 26 as tissue marking dye 27 flows into the pad 30.

Figure 8:
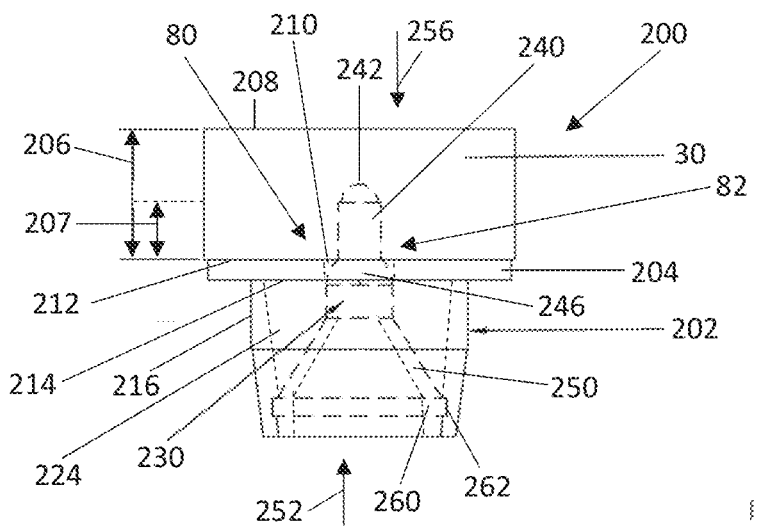
FIG. 8 is a schematic view of an applicator valve assembly of the applicator of FIG. 6.

With reference to FIG. 8, the applicator 14 may include an applicator valve assembly 200 that includes the pad 30 and the valve 80. The valve 80 controls flow of the tissue marking dye 27 from the reservoir 26 to the pad 30. In one form, the applicator valve assembly 200 includes a valve body 202 having a base 204 to which the pad 30 is mounted. The pad 30 may be mounted to the base 204 via adhesive or fasteners as some examples. The pad 30 may have a cylindrical shape and may be made of a porous material such as foam. The base 204 has an annular shape with an outer diameter the same size or slightly smaller than an outer diameter of the pad 30. The pad 30 has an initial height 206 that may decrease to a compressed height 207 when the distal surface 208 of the pad 30 is pressed against the flat surface 72 of the wall 52. Once the pressure against the distal surface 208 has been removed, the pad 30 may return from the compressed height 207 to the initial height 206.

The valve body 202 includes the port 82 through which the tissue marking dye may flow into the pad 30 from the reservoir 26. In one form, the port 82 includes an opening 210 of the base 204 that extends from an outer surface 212 of the base 204 to an inner surface 214 of the base 204. The valve body 202 includes a plug portion, such as an annular wall 216, depending from the base 204 and sized to fit in the socket 180. The annular wall 216 may be secured to the socket 180 using adhesive or a welding procedure, as some examples. In another embodiment, the valve body 204 has a unitary, one-piece construction so that the base 204 and annular wall 216 are integrally formed. The valve body 202 includes a cavity 224 upstream of the opening 210.

The valve 80 includes a valve member 230 and a valve seat, such as the base 204, which the valve member 230 engages to selectively inhibit flow of the tissue marking dye 27 through the opening 210. In one form, the valve member 230 includes an actuator pin 240 having a rounded end 242. The actuator pin 240 includes an outer diameter that is smaller than an inner diameter of the opening 210 to permit dye to flow through the opening 210 when the actuator pin 240 is disposed in the opening 210. The valve member 230 includes a valve element portion 246 that is sized to obstruct the opening 210 and inhibit the flow of the tissue marking dye 27 through the opening 210 when the valve element portion 246 is disposed in the opening 210. The valve member 230 may further include a spring portion 250 that resiliently urges the actuator pin 240 and valve element portion 246 in direction 252 to close the opening 210.

In one form, the valve member 230 has an integral, one-piece construction and may be a deformable plastic element with a slotted frustoconical spring portion 250 and a tapered valve element portion 246. The slotted, frustoconical spring portion 250 deforms in response to the rounded end 242 of the actuator pin 240 being urged in direction 256 as the pad distal surface 208 is pressed against a surface, such as the inner surface 72 of the well 52. Urging of the actuator pin 240 in direction 256 deforms the spring portion 250 and shifts the valve element portion 246 in direction 256 at least partially out of the opening 210 to permit tissue marking dye 27 to travel through the opening 210 and into the pad 30. In one form, the valve member 230 has a protrusion 260 that engages a groove 262 of the valve body 202 to secure the valve member 230 relative to the valve body 204.

The pad 30 may be made of a foam material that permits the tissue marking dye 27 to permeate through the pad 30 and is deformable to conform to the topography of a tissue sample. The actuator pin 240 is embedded in the pad 30 such that the pad 30 transfers force imparted against the distal surface 208 of the pad 30 to the actuator pin 240. The pad 30 thereby permits the surgeon to open the valve 80 by pressing the pad 30 against the inner surface 72 of the tray well 52 while being deformable enough to conform to a surface of a tissue sample to transfer tissue marking dye 27 to the tissue sample surface.

The system 10 may include additional instruments for marking a tissue sample. For example, the tray 18 may include a compartment that receives or more q-tips that a surgeon may use to remove excess tissue marking dye from a tissue sample.

A method of marking a tissue sample using the tissue marking system 10 will now be discussed. The method includes providing one or more of the systems 10. If multiple systems 10 are provided, each system 10 may include an applicator 14 having a different color tissue marking dye 27 as desired by the surgeon. For example, the method may include providing systems 10 including three or more of the following dye colors: black, blue, green, red, yellow, orange, violet, gold, teal, and magenta.

Before or after the tissue sample has been removed from the patient, systems 10 are positioned on a non-sterile support, such as a table at a periphery of an operating room. The containers 12 of the systems 10 are opened by separating the lids 16 from the trays 18. The following discussion refers to applying one color of the tissue marking dye 27 of one of the systems 10 to the tissue sample, but a similar approach will be used to apply the other colors of the tissue marking dye 27 of the other systems 10 to the tissue sample.

The user, such as a surgeon or a surgical technician, identifies the first desired tissue marking dye color and the associated applicator 14. The user grasps the applicator 14 with her fingers and lifts the applicator 14 out of the compartment 20. After removing the applicator 14 from the tray 18, the cap 22 is removed from the body 24 to expose the pad 30.

With reference to FIG. 9, the applicator 14 utilizes gravity to draw the tissue marking dye 27 out of the reservoir 26. The user holds the handle portion 92 to orient the body 24 so that the reservoir 26 is generally positioned above the pad 30.

The user advances the pad 30 in direction 300 into the well 52 with the longitudinal axis 173 of the applicator 14 extending transversely, such as perpendicular, to the longitudinal axis 175 of the compartment 20.

The user advances the pad 30 into the well 52 between the spaced wall portions 60, 62 of the compartment 20 and advances the distal surface 208 of the pad 30 into contact with the inner surface 72 of the base wall 70. With the pad distal surface 208 contacting the inner surface 72, the user shifts the body 24 in direction 300 toward the tray 18. This shifts the base 204 of the valve body 202 in direction 300 toward the well inner surface 72, compresses the pad 30, and shifts the actuator pin 240 in direction 256 (see FIG. 8) relative to the base 204. The shifting of the actuator pin 240 in direction 256 shifts the valve element portion 246 in direction 256 out of the opening 210. Because the valve element portion 246 no longer obstructs the opening 210, gravity can draw the tissue marking dye 27 out from the reservoir 26 and into the pad 30.

Once a desired amount of tissue marking dye has been applied to the pad 30, the user shifts the body 24 in direction 302 to withdraw the pad 30 from the well 52. When the distal surface 208 is no longer pressed against the well inner surface 72, the spring portion 250 of the valve member 230 urges the valve element portion 246 back in direction 252 into the opening 210. The valve element portion 246 closes the opening 210 and inhibits the flow of tissue marking dye 27 from the reservoir 26 into the pad 30. The applicator 14 thereby provides an accurate soaking of the pad 30 because the user simply shifts the body 24 in direction 302 to close the valve 80 once the desired amount of dye 27 has been applied to the pad 30. The user may determine that the pad 30 contains the desired amount of dye 27 once the user withdraws the pad 30 from the well 52 and visually observes that the pad 30 has left a mark of the tissue marking dye 27 on the well inner surface 72.

If the user wants additional tissue marking dye 27 on the pad 30, she again presses the pad 30 against the well inner surface 72 to open the valve 80 and cause tissue marking dye 27 to flow from the reservoir 26 to the pad 30. The user may repeatedly shift the body 24 up and down in directions 302, 300 two, three, or more times to repeatedly press the pad 30 against the well inner surface 72, open the valve 80, and saturate the pad 30. The repeated pressing permits dye 27 to flow out through the opening 210 and air to flow in through the opening 210 to take the place of the discharged tissue marking dye 27.

With the pad 30 adequately loaded with tissue marking dye 27, the surgeon applies the tissue marking dye 27 against a first surface of the tissue sample by contacting the distal surface 208 of the pad 30 against the tissue sample surface. The tissue marking dye 27 in the pad 30 will transfer to the first surface of the tissue sample and mark the first surface with the color of the tissue marking dye 27 in the reservoir 26.

Once the first surface of the tissue sample has been marked, the surgeon may place the applicator 14 back into the compartment 20 of the tray 18 and the tray 18 with applicator 14 therein may be disposed of.

The process is repeated to apply the other tissue marking dye colors of the other systems 10 to the surfaces of the tissue sample. For example, three systems 10 may be used to apply three different color dyes to three surfaces of a tissue sample. As another example, six systems 10 may be used to apply six different color dyes to six surfaces of a tissue sample.

It will be appreciated that various modifications to the system 10 may be utilized for different applications. For example, the container 10 may take the form of a flexible bag and the well 52 may be provided as a cup-shaped member contained in the bag with the applicator 14. As another example, the reservoir 26 may contain other marking fluids besides dye, such as ink, paint, and stains.

Figure 10:
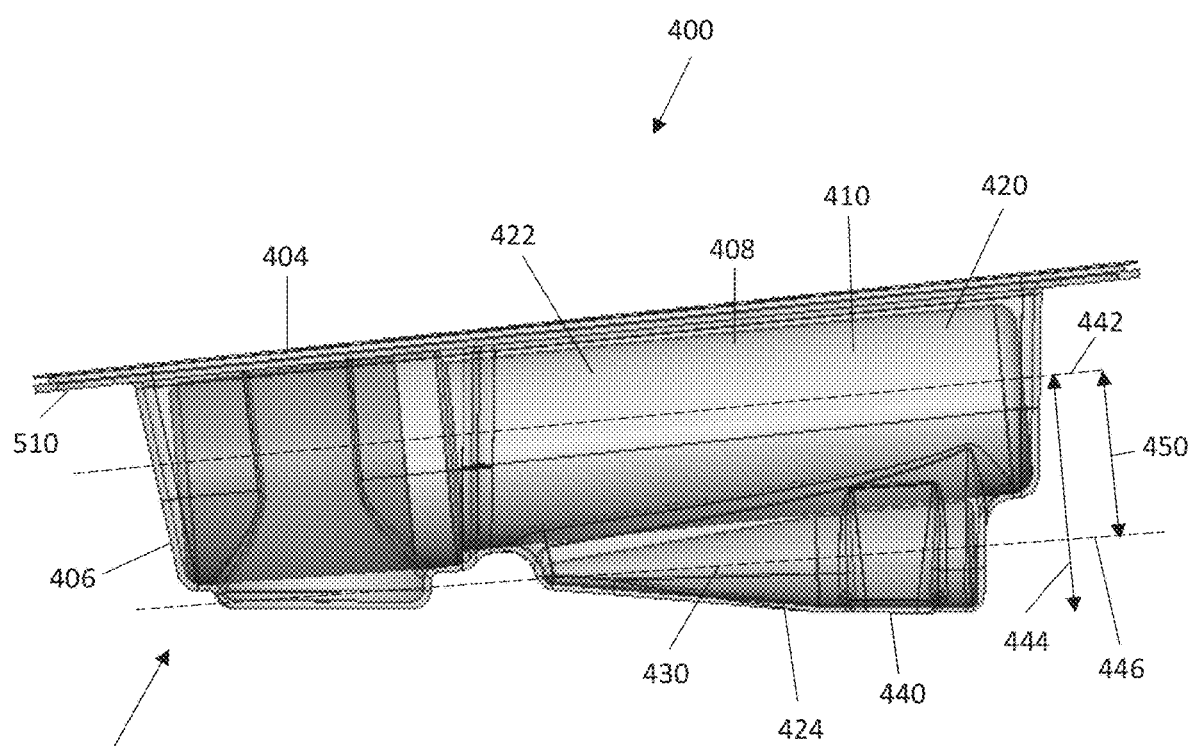
FIG. 10 is a side elevational view of a tissue marking system including a container, a tissue marking dye applicator, and a fine tip tissue marking dye applicator.

With reference to FIG. 10, a tissue marking system 400 is provided that is similar in many respects to the tissue marking system 10 discussed above. The tissue marking system 400 includes a container 402 that includes a lid 404 sealed to a tray 406. The tray 406 includes a compartment 408 that receives a primary applicator, such as an applicator 410, which is identical to the applicator 14 discussed above. The applicator 410 may include indicum 412 (see FIG. 11) such as words and colors indicating the color of the sterile tissue marking dye contained within the applicator 410. Further, the applicator 410 may include a lid 414 that is a color (e.g., yellow) representative of the color of the tissue marking dye contained in the applicator 410.

Figure 11:
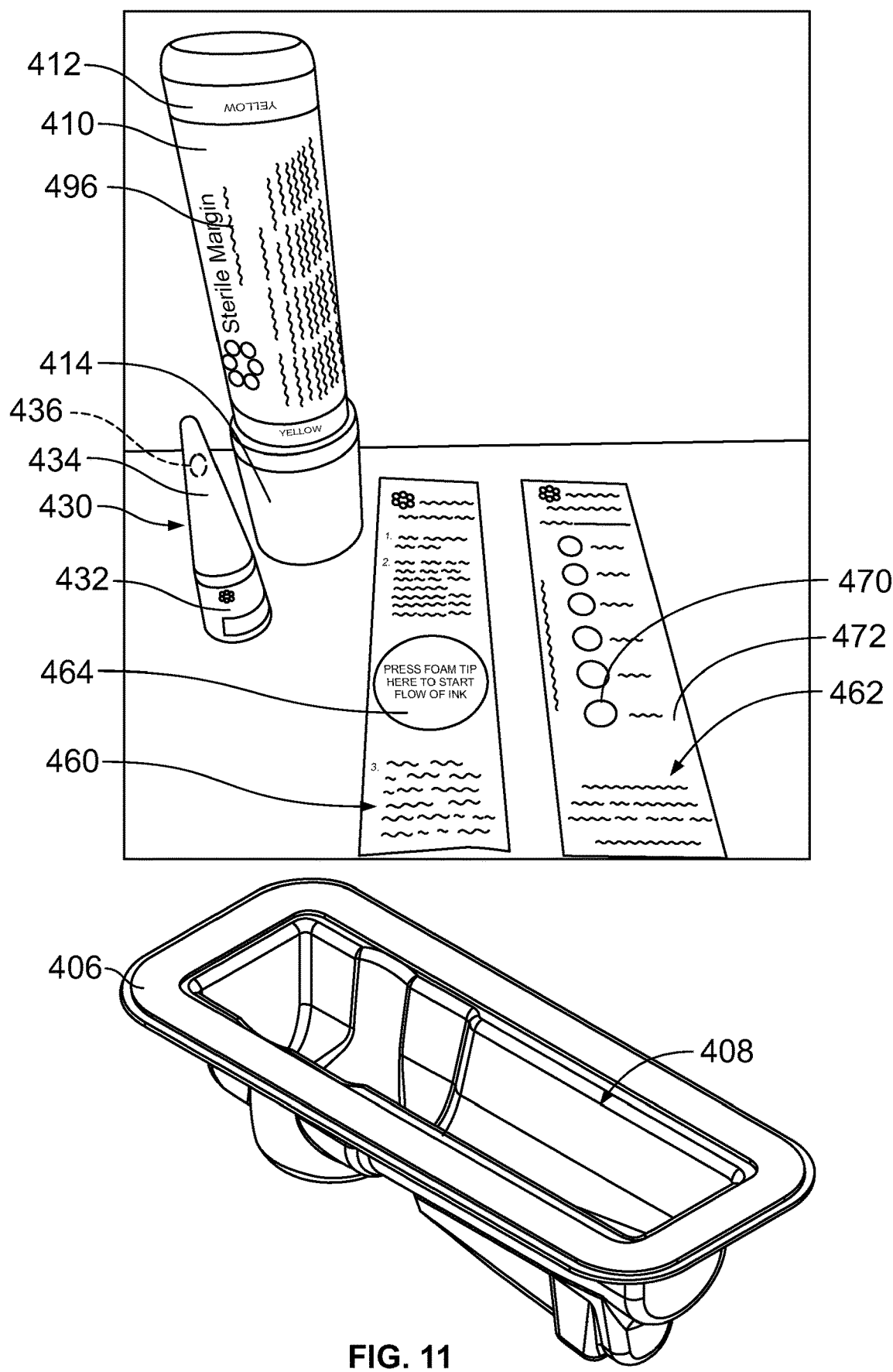
FIG. 11 is a perspective view of components of the tissue marking system of FIG. 11 including the tissue marking dye applicator, the fine tip tissue marking dye applicator, the tray, a priming card, and a color map.

The compartment 408 includes an upper applicator sub-compartment 420 that receives the applicator 410. The compartment 408 also includes a lower fine applicator sub-compartment 424 below the upper applicator sub-compartment 420. The tissue marking system 400 includes a secondary applicator, such as a fine tip applicator 430, having a body 432 (see FIG. 11) that contains tissue marking dye. The tissue marking dye of the fine tip applicator 430 may be the same color or a different color than the tissue marking dye of the applicator 410. Referring to FIG. 11, the fine tip applicator 430 includes a lid 434 threadedly connected to the body 432 and which covers a fine tip 436 of the fine tip applicator 430. The fine tip 436 may include a foam pad or bristles, as some examples.

Regarding FIG. 10, the compartment 408 supports the applicator 410 at an angle 444 relative to a bottom 440 of the tray 406. For example, the applicator 410 has a central axis 442 and the compartment 408 orients the central axis 442 to extend at an angle 444 relative to the bottom 440. The fine tip applicator 430 includes a central longitudinal axis 446. The compartment 408 permits the applicator 410 and fine tip applicator 430 to be stacked within the compartment 408 and orients the central longitudinal axis 442, 446 to extend at an angle 450 relative to each other. The over-under or stacked orientation of the applicator 410 and the fine tip applicator 430 permits both applicators 410, 430 to be received within the tray 406 while preserving a narrow footprint of the tray 406.

With reference to FIGS. 10 and 11, the tissue marking system 400 includes a substrate, such as a priming card 460, and a color map 462 that are positioned between the applicator 410 and the lid 404 when the lid 404 is sealed to the tray 406. Thus, when a user peels off the lid 404, the priming card 460 and the color map 462 may be removed from the compartment 408 by the user. The tissue marking system 400 may be sterilized, such as by gamma irradiation. The gamma irradiation sterilizes the applicator 410, the fine tip applicator 430, the priming card 460, the color map 462, and the interior surfaces of the lid 404 and tray 406. Because the tissue marking system 400 will be brought into an operating room, the outer surfaces of the lid 404 and tray 406 are not considered sterile for operating room purposes. However, the user may remove the lid 404 from the tray 406 at a nonsterile location, such as on a table at a periphery of an operating room, then tip the tray 406 upside down above a sterile surface, such as a tray near a surgical field, to remove the applicator 410, fine tip applicator 430, priming card 460, and color map 462 from the tray 406. The user could alternatively manually remove each component from within the compartment 408 as desired and position the components on the sterile surface without tipping over the tray 406.

The priming card 460 includes a priming area 464 against which a user may press a pad of the applicator 410 thereagainst to prime the applicator 410 and cause tissue marking dye to travel into the pad. The pad of the applicator 410 is identical to the pad 30 discussed above with respect to the applicator 14 (see FIG. 6). The instructions or color map 462 includes colors 470 and suggested margins 472 for each of the colors 470. This provides a readily understood key for applying differently colored tissue marking dyes to the margins of a tissue sample. For example, a surgeon may be provided with six tissue marking systems 400 each containing sterile tissue marking dye of one of the following colors: yellow, black, orange, red, green, and blue. The surgeon uses the color map 462 of one of the tissue marking systems 400 to select which color to apply to the margins of a tissue sample. In one embodiment, the color map 462 instructs yellow dye to be applied to the anterior margin, black dye to be applied to the posterior margin, orange dye to be applied to the lateral margin, red dye to be applied to the medial margin, green dye to be applied to the inferior margin, and blue dye to be applied to the superior margin.

Figure 12:
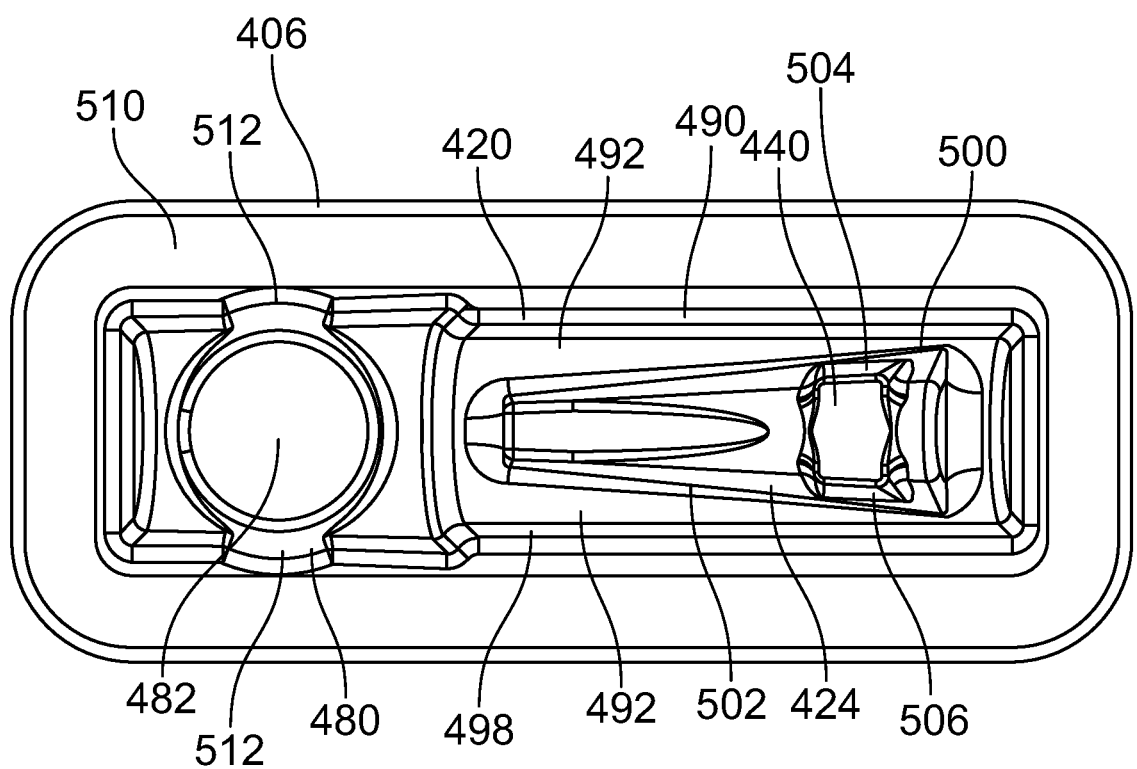
FIG. 12 is a top plan view of the tray of FIG. 11 showing a smaller sub-compartment that receives the fine tip tissue marking dye applicator and a larger sub-compartment that receives the tissue marking dye applicator.

With reference to FIG. 12, the tray 406 is similar in many respects to the tray 18 discussed above. For example, the tray 406 includes a well 480 having a floor 482. The tissue marking system 400 provides flexibility to a user because the user may use either the priming area 464 of the priming card 460 or the well floor 482 of the tray 406 to prime the applicator 410 and cause sterile tissue marking dye to flow into the pad of the applicator 410. The upper applicator sub-compartment 420 includes a sidewall 490 that includes inwardly curving portions 492 that are configured to support a handle portion 496 (see FIG. 11) of the applicator 410. The inwardly curving portions 492 lead downward from an upper opening 498 of the upper applicator sub-compartment 420 to an opening 500 of the lower fine applicator sub-compartment 424. The lower fine applicator sub-compartment 424 includes a side wall 502 extending downward toward the bottom 440 of the tray 406. The side wall 502 includes recesses 504, 506 that provide clearance for a user to insert her fingers into the lower fine applicator sub-compartment 424 on opposite sides of the fine tip applicator 430 to remove the fine tip applicator 430 from the lower fine applicator sub-compartment 424. The opening 500 is smaller than the upper opening 498 so that the fine tip applicator 430 may pass through the opening 500 and into the lower fine applicator sub-compartment 424 while the applicator handle portion 496 rests against the inwardly curving portions 492 of the upper applicator sub-compartment 420 and does not enter into the lower fine applicator sub-compartment 424.

Figure 13:
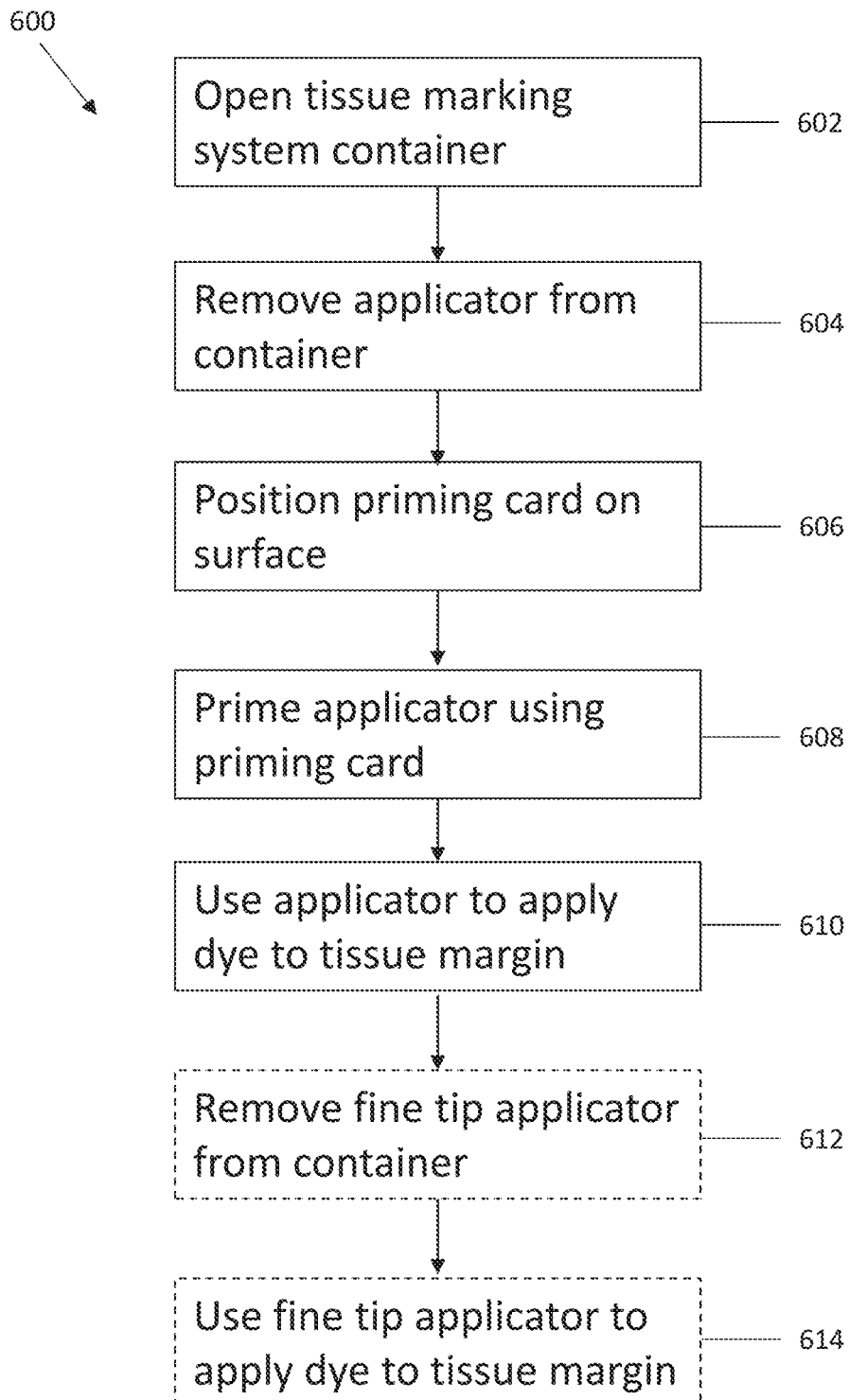
FIG. 13 is a flow chart showing a method of using the tissue marking system of FIG. 10 to apply tissue marking dyes to a margin of a tissue sample.

With reference to FIG. 13, a method 600 is provided for applying sterile tissue marking dye to one or more margins of a tissue sample using the tissue marking system 400. The method 600 includes opening 602 the tissue marking system container 402. In one form, the opening 602 includes peeling the lid 404 off of a flange 510 (see FIG. 12) of the tray 406.

The method 600 includes removing 604 the applicator 410 from the container 402. The user may remove the applicator 410 from the container 604 by inserting fingers into recesses 512 (see FIG. 12) on opposite sides of the lid 414 of the applicator 410 and lifting the applicator 410 out of the upper applicator sub-compartment 408.

The method 600 includes positioning 606 the priming card 460 on a surface. The surface may be a sterile surface within an operating room, such as a tray near the operating field. The method 600 further includes priming 608 the applicator 410 using the priming card 460. A user may prime 608 the applicator 410 by positioning the pad of the applicator 410 against the priming area 464 and shifting the handle portion 496 toward the priming card 460 which opens a valve within the applicator 410. The open valve permits the tissue marking dye within the applicator 410 to flow into the pad of the applicator 410. The opening of the valve within the applicator 410 is similar to the applicator priming operation discussed above with respect to applicator 14.

Once the pad of the applicator 410 is sufficiently saturated with tissue marking dye, the method 600 includes using 610 the applicator 410 to apply tissue marking dye to a margin of a tissue sample.

The method 600 may further include removing 612 the fine tip applicator 430 from the container 402. In one approach, the removing 612 includes a user advancing her fingers into the recesses 504, 506 on opposite sides of the fine tip applicator 430. The user may then lift the fine tip applicator 430 out of the lower fine applicator sub-compartment by withdrawing the fine tip applicator 430 through the opening 500 and the upper opening 498.

The method 600 may also include using 614 the fine tip applicator 430 to apply sterile tissue marking dye to a tissue margin. As discussed above, the sterile tissue marking dye within the fine tip applicator 430 may be the same color as the sterile tissue marking dye in the applicator 410. If the sterile tissue marking dyes in the applicators 410, 430 are the same color, the steps 610, 614 involve marking different portions of the same margin of the tissue sample. For example, the fine tip applicator 430 may be used to apply dye to small areas of a tissue margin that were difficult to adequately cover with dye from the applicator 410. If the sterile tissue marking dyes in the applicators 410, 430 are different colors, the steps 610, 614 involve marking different margins of the tissue sample.

While there have been illustrated and described particular embodiments of the present invention, it will be appreciated that numerous changes and modifications will occur to those skilled in the art, and it is intended for the present invention to cover all those changes and modifications which fall within the scope of the appended claims.

What is claimed is:

1. A tissue marking system for marking a tissue specimen, the tissue marking system comprising:
   a sealed container having a sterile interior;
   a sterile elongate applicator in the sterile interior of the sealed container, the elongate applicator having a longitudinal axis, the entirety of the elongate applicator in the sterile interior of the sealed container;
   wherein the sealed container is openable to remove the applicator from the sterile interior of the sealed container;
   the elongate applicator comprising:
      a body having a closed end portion and an open end portion opposite the closed end, the open end portion of the body having a body opening;
      an internal reservoir of the body containing sterile tissue marking dye; and
      an applicator valve assembly connected to the open end portion of the body, the applicator valve assembly comprising:
         a pad;
         a valve body comprising:
            a base supporting the pad and having a base opening;
            a support member depending from the base and extending into the body opening of the body; and
         a valve member comprising:
            a valve element portion shiftable along the longitudinal axis between a closed position wherein the valve element portion obstructs the base opening to keep the tissue marking dye in the internal reservoir of the body and an open position wherein the valve element portion permits the tissue marking dye to travel from the internal reservoir of the body, through the base opening, and into the pad;
            an actuator pin portion projecting from the valve element portion and having a free end positioned to be contacted by the pad upon the pad being pressed against a surface, the actuator pin portion configured to shift the valve element portion along the longitudinal axis from the closed position to the open position upon the actuator pin portion being contacted by the pad; and
            a frustoconical spring portion connecting the valve element portion to the support member of the valve body and biasing the valve element portion toward the closed position, the frustoconical spring portion deforming in response to the valve element portion being shifted axially from the closed position toward the open position by the actuator pin portion.

2. The tissue marking system of claim 1 further comprising a substrate that includes a priming surface, the substrate being removable from the sealed container.

3. The tissue marking system of claim 1 wherein the sealed container includes a tray having a compartment and a lid secured to the tray; and
   a card in the compartment of the tray, the card including a priming surface and being removable from the compartment of the tray.

4. The tissue marking system of claim 1 wherein the sealed container includes a well sized to receive the tip of the applicator and a base wall of the well that includes a priming surface.

5. The tissue marking system of claim 4 wherein the well of the container includes at least one wall upstanding from the base wall to resist egress of sterile tissue marking dye from the well.

6. The tissue marking system of claim 1 further comprising a fine-tip applicator in the sealed container.

7. The tissue marking system of claim 6 wherein the sealed container includes a tray having a compartment, the applicator being above the fine-tip applicator in the compartment.

8. The tissue marking system of claim 1 wherein the pad is porous.

9. The tissue marking system of claim 1 wherein the applicator includes a cap connected to the body and covering the pad.

10. A tissue marking system comprising:
   a sealed container and an elongate applicator in the sealed container, the elongate applicator having a longitudinal axis;
   the sealed container comprising:
      a tray comprising:
         an internal compartment;
         an opening in communication with the internal compartment;
         a flange extending about the opening;
      a lid connected to the flange of the tray and covering the opening of the tray;
   the elongate applicator in the internal compartment of the tray of the sealed container, the elongate applicator comprising:
      an elongate body having a closed end portion, an open end portion opposite the closed end portion, an interior containing tissue marking dye, and a tubular side wall extending about the interior of the body;
      an applicator valve assembly connected to the open end portion of the elongate body, the applicator valve assembly comprising:
         a pad;
         a base having an upper surface and a lower surface opposite the upper surface, the pad above the upper surface of the base;
         a through opening of the base extending between the upper and lower surfaces of the base;

a lower valve element shiftable along the longitudinal axis between a closed position and an open position, wherein the lower valve element in the closed position thereof is configured to obstruct the through opening of the base and inhibit tissue marking dye in the interior of the elongate body from flowing through the through opening of the base to the pad;

an upper actuator protruding from the lower valve element and axially shiftable therewith, the upper actuator having a free end above the upper surface of the base and adjacent the pad with the lower valve element in the closed position thereof, the upper actuator being configured to shift the lower valve element from the closed position to the open position in response to the pad being pressed against a surface; and a resilient member configured to bias the lower valve element axially upward toward the closed position and resiliently deform in response to the upper actuator shifting the lower valve element downward from the closed position toward the open position.

11. The tissue marking system of claim 10 wherein the internal compartment comprises an upper applicator sub-compartment and a lower applicator sub-compartment below the upper applicator sub-compartment; and wherein the applicator is in the upper applicator sub-compartment of the tray, the tissue marking system further comprising:

a fine applicator in the lower applicator sub-compartment so that the applicator and the fine applicator are vertically aligned in the sealed container;

wherein the fine applicator contains tissue marking dye and includes a fine tip.

12. The tissue marking system of claim 11 wherein the fine applicator includes a body and a lid connected to the body.

13. The tissue marking system of claim 11 wherein the applicator includes a cap removably connected to the body and protecting the pad.

14. The tissue marking system of claim 10 wherein the internal compartment of the tray includes a well having a base wall including a priming surface and at least one wall upstanding from the base wall and defining an opening of the well, the opening of the well having a distance thereacross sized to permit the pad to be advanced into the opening of the well and contact the priming surface.

15. The tissue marking system of claim 10 further comprising a substrate that includes a priming surface, the substrate being removable from the sealed container.

16. The tissue marking system of claim 10 wherein the pad is porous.

17. The tissue marking system of claim 10 wherein the tray and the lid include sterile interior surfaces; and wherein the applicator is sterile.

18. The tissue marking system of claim 1 wherein the frustoconical spring portion comprises a slotted frustoconical member.

19. The tissue marking system of claim 1 wherein the frustoconical spring portion and the support member comprise an engaged protrusion and groove.

20. The tissue marking system of claim 1 wherein the support member comprises an annular wall.

21. The tissue marking system of claim 1 wherein the valve element portion, actuator pin portion, and frustoconical spring portion have a unitary, one-piece construction.

22. The tissue marking system of claim 10 wherein the open end portion of the body includes a socket; and wherein the base of the applicator valve assembly includes a plug portion extending in the socket of the body.

* * * * *